US010231968B2

(12) United States Patent
Hardten et al.

(10) Patent No.: US 10,231,968 B2
(45) Date of Patent: Mar. 19, 2019

(54) MEDICINAL SOLUTION TO BE CONTINUOUSLY OR PULSE-DELIVERED TO THE EYE FOR TREATING OPHTHALMOLOGICAL CONDITIONS/MALADIES

(71) Applicants: David R. Hardten, Excelsior, MN (US); Richard L. Lindstrom, Wayzata, MN (US)

(72) Inventors: David R. Hardten, Excelsior, MN (US); Richard L. Lindstrom, Wayzata, MN (US)

( * ) Notice: Subject to any disclaimer, the term of this patent is extended or adjusted under 35 U.S.C. 154(b) by 0 days.

(21) Appl. No.: 15/224,695

(22) Filed: Aug. 1, 2016

(65) Prior Publication Data

US 2018/0028533 A1    Feb. 1, 2018

(51) Int. Cl.
| | | |
|---|---|---|
| C07D 475/14 | (2006.01) | |
| A61K 31/4985 | (2006.01) | |
| A61K 9/08 | (2006.01) | |
| A61K 9/00 | (2006.01) | |
| A61K 47/02 | (2006.01) | |
| A61K 47/18 | (2017.01) | |
| A61K 31/4174 | (2006.01) | |
| A61K 31/4178 | (2006.01) | |
| A61K 38/14 | (2006.01) | |
| A61K 31/357 | (2006.01) | |
| A61K 31/407 | (2006.01) | |
| A61K 31/573 | (2006.01) | |

(52) U.S. Cl.
CPC ........ *A61K 31/4985* (2013.01); *A61K 9/0048* (2013.01); *A61K 9/08* (2013.01); *A61K 31/357* (2013.01); *A61K 31/407* (2013.01); *A61K 31/4174* (2013.01); *A61K 31/4178* (2013.01); *A61K 31/573* (2013.01); *A61K 38/14* (2013.01); *A61K 47/02* (2013.01); *A61K 47/186* (2013.01)

(58) Field of Classification Search
None
See application file for complete search history.

(56) References Cited

U.S. PATENT DOCUMENTS

| | | |
|---|---|---|
| 6,242,447 B1 | 6/2001 | Demopulos et al. |
| 6,254,585 B1 | 7/2001 | Demopulos et al. |
| 6,261,279 B1 | 7/2001 | Demopulos et al. |
| 6,413,961 B1 | 7/2002 | Demopulos et al. |
| 6,420,432 B2 | 7/2002 | Demopulos et al. |
| 7,973,068 B2 | 7/2011 | Demopulos et al. |
| 8,173,707 B2 | 5/2012 | Demopulos et al. |
| 8,586,633 B2 | 11/2013 | Demopulos et al. |
| 8,945,101 B2 | 2/2015 | Herekar et al. |
| 9,254,271 B2 | 2/2016 | Demopulos et al. |
| 9,278,101 B2 | 3/2016 | Demopulos et al. |
| 9,295,685 B2 | 3/2016 | Gombotz et al. |
| 2007/0269379 A1 | 11/2007 | Mitragotri et al. |
| 2010/0286156 A1 | 11/2010 | Pinelli |
| 2011/0117070 A1 | 5/2011 | Aurora et al. |
| 2015/0335704 A1* | 11/2015 | Karolchyk ............. A61K 38/14 |

FOREIGN PATENT DOCUMENTS

WO    WO 2015/138794    9/2015

OTHER PUBLICATIONS

Latreille, Anal Bioanal Chem (2015) 407:3567-3578 (Year: 2015).*
Morand, International Journal of Pharmaceutics 344 (2007) 150-153 (Year: 2007).*
https://www.promises.com/articles/drugs-cause-pupils-constrict/ (Year: 2017).*
Trose, Pharm. Prax., 43, No. 3, 109-11, 1988 (Year: 2017).*
Bottós, Arq Bras Oftalmol. 2011; 74(5):348-51 (Year: 2011).*

* cited by examiner

*Primary Examiner* — Satyanarayana R Gudibande
(74) *Attorney, Agent, or Firm* — Law Offices of Steven W. Weinrieb

(57) ABSTRACT

The present invention relates generally to a medicinal solution, and more particularly to a medicinal solution which is to be continuously or pulse-delivered for the purpose of treating various ocular diseases, conditions, or maladies, such as keratoconus, infectious keratitis, severe inflammatory conditions, and ocular surface neoplasia. In particular, the medicinal solution comprises the combination of a medication for treating one of the aforenoted or similar diseases, conditions, or maladies, and an anesthetic for rendering the patient comfortable during the treatment procedure.

18 Claims, 5 Drawing Sheets

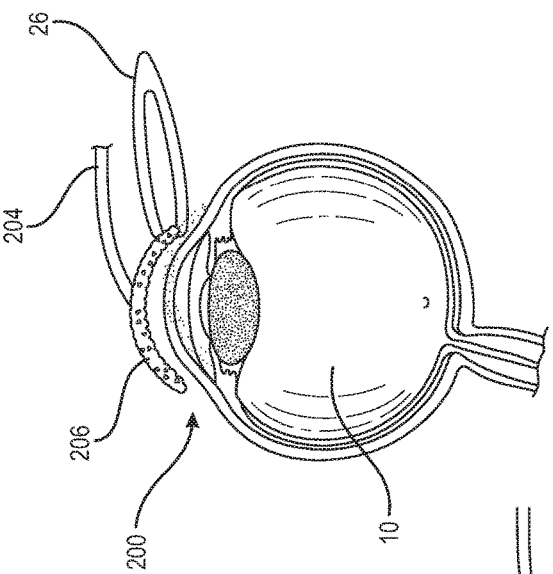
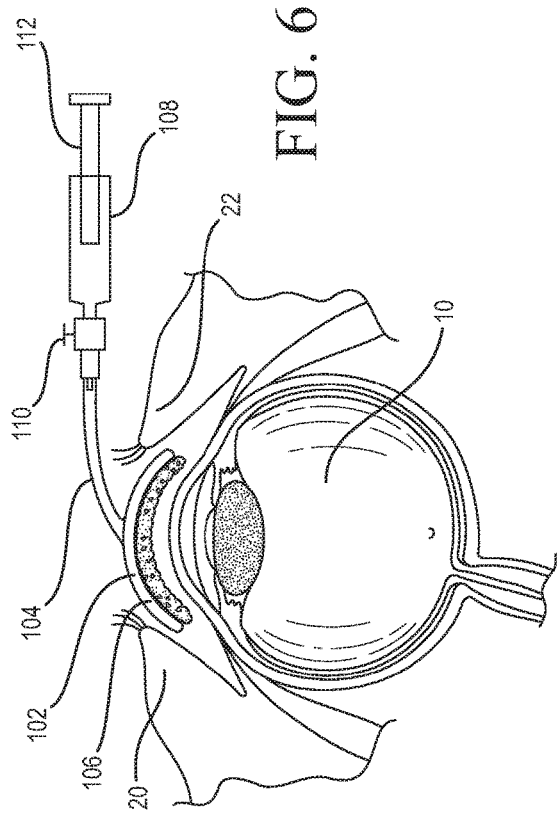
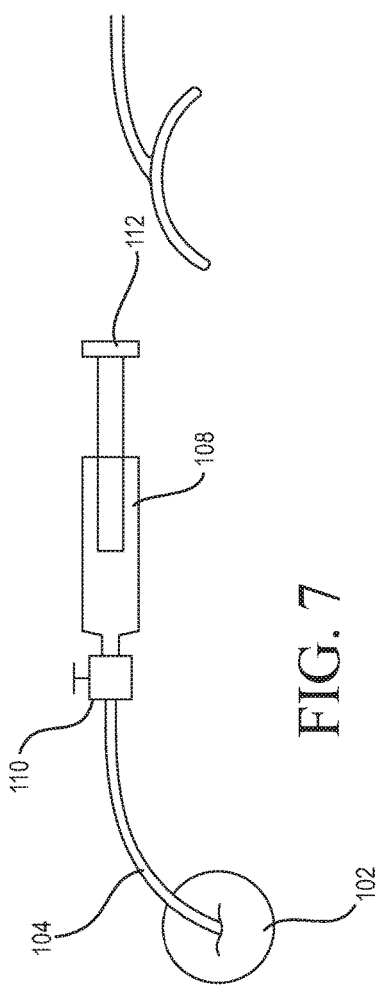
FIG. 6
FIG. 7
FIG. 8

MEDICINAL SOLUTION TO BE CONTINUOUSLY OR PULSE-DELIVERED TO THE EYE FOR TREATING OPHTHALMOLOGICAL CONDITIONS/MALADIES

FIELD OF THE INVENTION

The present invention relates generally to a medicinal solution, and more particularly to a medicinal solution which is to be continuously or pulse-delivlered to the eye for the purpose of treating various corneal conditions such as, for example, keratoconus wherein corneal collagen cross-linking techniques are employed in connection with the photosensitizing of the human cornea with ultraviolet-A rays in the presence of oxygen order to strengthen the cornea, as well as other corneal diseases, such as, for example, infectious keratitis, severe inflammatory conditions, and ocular surface squamous neoplasia.

BACKGROUND OF THE INVENTION

When treating various corneal conditions, such as, for example, keratoconus wherein corneal collagen crosslinking techniques are employed in connection with the photosensitizing of the human cornea with ultraviolet-A rays in order to strengthen the cornea, as well as other corneal diseases, such as, for example, infectious keratitis, severe inflammatory conditions, and ocular surface squamous neplasia, various solutions are required to be supplied to or cause the eye to be bathed within such solutions for a predetermined period of time. Riboflavin is a topical medication that is conventionally used for the purposes of corneal saturation in connection with corneal collagen crosslinking, and prior to the delivery of ultraviolet light to the cornea, so as to effectively increase the strength of the cornea and thereby treat keratoconus. The cornea can be weakened by various corneal diseases, one of which is keratoconus, which is a debilitating condition that is progressively degenerative, often bilateral, and can cause vision distortion, with multiple images, and sensitivity to light in early stages, and even blindness in more severe cases. When an eye develops keratoconus, the cornea becomes thinned and unstable, and in lieu of retaining its domed shape covering the front the eye, the cornea becomes more cone-shaped, thereby bending the light coming into the eye, in an unnatural manner, and thus leading to the aforenoted vision distortion problems. Sometimes, a corneal transplant is required.

Conventional treatment of keratoconus comprises the delivery of riboflavin to the affected cornea, and one conventional procedure may initially entail the removal of the epithelium or outermost layer of the cornea, or alternatively, the epithelium may be permitted to remain intact. In the past, it was preferred to remove the epithelium, the thinking or belief in the ophthalmological medical field being that better results could be achieved because the riboflavin would be more easily and more quickly absorbed by the cornea which, in turn, would lead to better treatment results. Current thinking or belief in the field, however, is that leaving the epithelium intact may be somewhat safer in that the epithelium layers does in fact provide an extra protective layer to the cornea, and that the end results achieved are basically the same as compared to those results achieved when the epithelium layer has been initially removed. In either case, riboflavin is applied to the eye, and after a predetermined period of time, which may vary from anywhere between five and forty-five minutes, the crosslinking techniques are begun by photosensitizing the cornea with ultraviolet light. It has been found that the ultraviolet light photosensitizing procedures can vary depending upon, for example, various protocols or variables. For example, the ultraviolet light may be applied continuously or in pulses. Alternatively, different concentrations of the light can also be employed. Conventionally, the photosensitizing procedures usually comprise time frames which may vary anywhere from between two and thirty minutes. In accordance with some prior art conventional solutions and techniques, various solutions have been proposed whereby such solutions resulted in enhanced retention times upon the cornea being achieved. Still other prior art conventional solutions have effectively been utilized to break down the epithelial layer or barrier of the cornea so as to facilitate enhanced penetration of the solutions into the cornea.

Regardless of which type of medications were being used, and regardless of whether or not the epithelial layer or barrier was removed or permitted to remain intact, it is also known that the intermittent delivery of topical anesthetic solutions to the patient has been required in order to ensure the patient's comfort throughout the procedure. This is also true in the case where other corneal diseases, conditions, or maladies such as, for example, infectious keratitis, severe inflammatory conditions, and ocular surface neoplasia, are also being treated by means of medications other than riboflavin such as, for example, suitable anti-infectives, anti-inflammatories, or anti-neoplasia agents. However, it can also be readily appreciated that in view of the fact that the application of the delivery of the topical anesthetic solutions to the eye, in connection with the treatment of any of the foregoing conditions, is intermittently performed, whereby the delivery of the particular medication will likewise necessarily be intermittent, the overall treatment process or procedure becomes substantially timely and labor-intensive in view of the additional fact that such procedures must be performed by trained medical personnel, and therefore, such treatment processes or procedures become relatively expensive. Furthermore, many of the medication or fluid application procedures require the patient to maintain his or her head in a predetermined position, or to maintain the eyes in a fixed mode, such as, for example, looking straight ahead, or still further, to have their eyelids held open for relatively long periods of time. All of these procedures may result in some level of discomfort to the patient, which is obviously not ideal. Accordingly, it would be desirable if a medicinal solution could be developed which would require less frequent human intervention and, at the same time, would effectively and simultaneously provide the maximum degree of comfort to the patient.

A need therefore exists in the art for a new and improved medicinal solution to be delivered to the eye that will resolve the aforenoted problems or drawbacks characteristic of the current state of the art and that will achieve the following overall objectives. More particularly, a need exists in the art for a new and improved medicinal solution to be delivered to the eye which will be cost effective, which will be significantly more comfortable for the patient, which eliminate the need for intermittent intervention procedures to be performed by medical personnel in connection with both the delivery of the medicinal solution for the actual treatment of the particular eye condition as well as the necessarily attendant anesthetic in order to render the patient as comfortable as possible, and which will enable a sufficient amount of medication or fluid to effectively be constantly or continuously delivered or applied to the eye.

OVERALL OBJECTIVES OF THE INVENTION

The overall objectives of the present invention are to overcome the drawbacks characteristic of, and encountered during, current procedures, techniques, or methods for applying various medications or fluids to a patient's eye, to provide a medicinal solution to be applied to a patient's eye that is significantly more comfortable for the patient being treated, and to enhance the efficiency and effectiveness of the medication or fluid delivery to the patient's eye as well as to constantly retain a predetermined amount of the medication or fluid upon the eye throughout the entire treatment procedure.

SUMMARY OF THE INVENTION

The foregoing and other objectives are achieved in accordance with the teachings and principles of the present invention through the provision of a new and improved medicinal solution which comprises the combination of an ocular medication, for the treatment of a particular ocular condition, disease, or malady, and an anesthetic which will provide comfort to the patient's eye while not diluting the treatment medication. The medicinal solution of the present invention is to be used in conjunction with treatment procedures where either the epithelium has been initially removed or permitted to remain intact. The medicinal solution of the present invention provides unique mixtures of medications not previously proposed, known, or utilized, and wherein the ratio of the medication can vary from trace amounts up to the saturation point of the medication within the mixture solution. The anesthetic can be any solution that causes corneal anesthesia or comfort, such as, for example, proparacaine, lidocaine, tetracaine, bupivacaine, non-steroidal medications, or any other substances with corneal anesthetic properties. Still further, any other medications can also be combined with the aforenoted medications in order to enhance the patient's comfort or the objectives of the treatment procedure, such as, for example, medications that would cause pupillary constriction such as pilocarpine or other miotic medications that would facilitate more comfort to the patient due to the lessening of light entering that part of the eye posterior to the iris, such as, for example, the lens or retina. The particular medications to be utilized may be medications to treat a variety of ocular conditions, diseases, or maladies such as, for example, keratoconus, infectious keratitis, severe inflammatory conditions, and ocular surface neoplasia.

BRIEF DESCRIPTION OF THE DRAWINGS

Various other features and attendant advantages of the present invention will be more fully appreciated from the following detailed description when considered in connection with the accompanying drawings in which like reference characters designate like or corresponding parts throughout the several views, and wherein:

FIG. 6 is a top plan view of the patient's eyeball, similar to that of FIG. 5, additionally showing a fluid injection syringe operatively connected to the free end portion of the irrigation fluid supply tube, and, for example, a stopcock valve operatively associated therewith so as to provide a predetermined volumetric supply and control of the flow of the medicinal solution to the corneal sponge;

FIG. 7 is an external plan view of a scleral lens having a single irrigation fluid supply tube and syringe/plunger/stopcock assembly operatively connected thereto at, for example, an axially central portion of the scleral lens;

FIG. 8 is a top plan view of the patient's eyeball, similar to that of FIG. 4, schematically illustrating a second embodiment of medicinal solution apparatus wherein the scleral contact lens has effectively been eliminated, wherein the irrigation fluid supply tube is fixedly connected directly to the sponge, and wherein further, the sponge, with the irrigation fluid supply tube connected thereto, is placed upon the patient's eye in a manner corresponding to that illustrated within FIGS. 3b,3c by means of the forceps;

DETAILED DESCRIPTION OF THE PREFERRED EMBODIMENT

Figure 1:
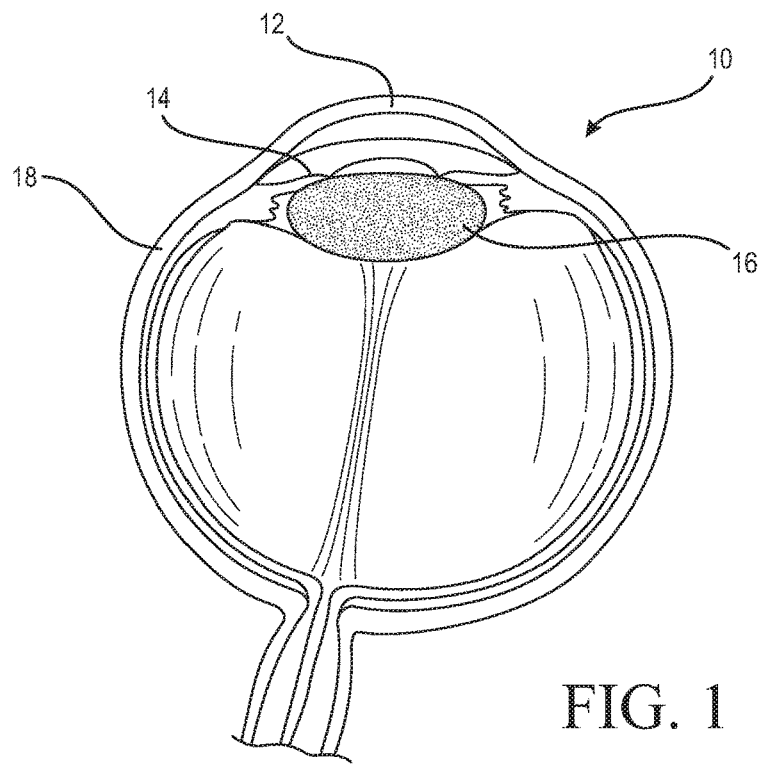
FIG. 1 is a schematic cross-section of the human eye showing, for example, among other components of the eye, the sclera and the cornea.

In accordance with the principles and teachings of the present invention, there is provided a new and improved medicinal solution which comprises the combination of a corneal treatment medication and an anesthetic which will provide comfort to the patient's eye while not diluting the treatment medication. The medicinal solution of the present invention is to be used in conjunction with treatment procedures where either the epithelium has been initially removed or permitted to remain intact. The medicinal solution of the present invention provides unique mixtures of medications not previously proposed, known, or utilized, and wherein the ratio of the medication can vary from trace amounts up to the saturation point of the medication within the mixture solution. The anesthetic can be any solution that causes corneal anesthesia or comfort, such as, for example, proparacaine, lidocaine, tetracaine, bupivacaine, non-steroidal medications, or any other substances with corneal anesthetic properties. Still further, any other medications can also be combined with the aforenoted medications in order to enhance the patient's comfort or the objectives of the treatment procedure, such as, for example, medications that would cause pupillary constriction such as pilocarpine or other miotic medications that would facilitate more comfort to the patient due to the lessening of light entering that part of the eye posterior to the iris, such as, for example, the lens or retina.

One medication that is used in connection with, for example, the treatment of keratoconus is riboflavin. Riboflavin exhibits photosensitizing capacities that, when exposed to ultraviolet light, can accumulate energy and cause a reaction in surrounding tissue, such as, for example, the cornea. Concentrations of riboflavin conventionally utilized in eye drops have typically been between 0.05% and 2.0%. As for the anesthetic component, amino ester topical anesthetics are those such as, for example, procaine, chloroprocaine, tetracaine, cocaine, and benzocaine. Amino amides that are used for topical anesthesia include dibucaine, lidocaine, mepivacaine, prilocaine, bupivacaine, levobupivacaine, ropivacaine, articaine, and etidocaine. It is to be noted that various combinations of the above anesthetics are useful in order to achieve a longer duration of anesthesia, or improved penetration of the same with respect to the various eye components, for various applications. Concentrations of the medications will vary. For example, for benzocaine, up to 20% (200 mg/ml) is often used for anesthesia. For lidocaine, variations of 1-4% (10-40 mg/ml) are often used. Concentrations of 0.3% to 1.0% for proparacaine have been commonly used, with 0.5% (5 mg/ml) being the most common. Likewise, concentrations of 0.5% (5 mg/ml) are also common for tetracaine. It is noted that the pH values of the various constituents may need to be adjusted so as to ensure comfort within the eye of the patient. Continuing further, the most common medication that causes pupillary constriction with topical use is pilocarpine and is usually used in concentrations between 0.5% and 4.0% (5 mg/ml to 40 mg/ml). Still yet further, there are many topical non-steroidal anti-inflammatory medications that also reduce discomfort of the eye, and these include diclofenac, ketorolac, flurbiprofen, nepafenac, and bromfenac. It is also noted that the eye can become red during treatment, and several medications that can be utilized in order to reduce such vascular congestion may be any one of phenylephrine, epinephrine, naphazoline, and pheniramine.

In addition to the use of, for example, riboflavin in connection with the treatment of keratoconus, this invention likewise includes the use of other medications, along with a suitable anesthetic, for the treatment of other ocular conditions, diseases, or maladies such as, for example, infectious keratitis, severe inflammatory conditions, and ocular surface neoplasia.

The following examples are submitted to be exemplary of medicinal solutions which have been formulated in accordance with the principles and teachings of the present invention, however, it is to be understood that such examples are not to be construed as limiting in any way in that still other medicinal solution formulations are possible:

Example 1

A first solution containing riboflavin may comprise a 1000 ml 0.01% to a 0.9% sodium chloride solution, with a 0.45% sodium chloride solution being preferred, comprising 1 mg to 10000 mg of riboflavin, with a preferred amount being 6000 mg of riboflavin, for a final concentration of 0.0001% to 1.0%, or a preferred concentration of 0.6%, 1 mg to 10000 mg of proparacaine or a similar anesthetic, with a preferred amount being 1000 mg of proparacaine, for a final concentration of 0.0001% to 1.0%, or a preferred concentration of 0.1%, 1 mg to 3000 mg of benzalkonium chloride or a similar preservative, with a preferred amount being 500 mg, for a final concentration of 0.0001% to 0.3%, or a preferred concentration of 0.05%, 1 mg to 500 mg of naphazoline hydrochloride or a similar vasoconstrictor, with a preferred amount being 50 mg, for a final concentration of 0.0001% to 0.05%, or a preferred concentration of 0.005%, and 1 mg to 40000 mg of pilocarpine hydrochloride or a similar miotic, with a preferred amount being 500 mg, for a final concentration of 0.0001% to 4.0%, or a preferred concentration of 0.005%.

Example 2

A second solution containing riboflavin may comprise a 1000 ml 0.01% to 0.9% sodium chloride solution, with a 0.45% sodium chloride solution being preferred, comprising 1 mg to 10000 mg of riboflavin, with a preferred amount of 5500 mg, for a final concentration of 0.0001% to 1.0%, or a preferred concentration of 0.55%, 1 mg to 10000 mg of proparacaine or a similar anesthetic, with a preferred amount being 500 mg of proparacaine, for a final concentration of 0.0001% to 1.0%, or a preferred concentration of 0.05%, and 1 mg to 3000 mg of benzalkonium chloride or a similar preservative, with a preferred amount of 250 mg of benzalkonium chloride, for a final concentration of 0.0001% to 0.3% or a preferred concentration of 0.025%.

Example 3

A third solution containing riboflavin may comprise a 1000 ml 0.01% to 0.9% sodium chloride solution, with a 0.45% sodium chloride solution being preferred, comprising 1 mg to 10000 mg of riboflavin, with a preferred amount being 2500 mg of riboflavin, for a final concentration of 0.0001% to 1.0%, or a preferred concentration of 0.25%, 1 mg to 10000 mg of proparacaine or a similar anesthetic, with a preferred amount being 750 mg of proparacaine, for a final concentration of 0.0001% to 1.0%, or a preferred final concentration of 0.075%, 1 mg to 3000 mg of benzalkonium chloride or a similar preservative, with a preferred amount being 100 mg of benzalkonium chloride, for a final concentration of 0.0001% to 0.3%, with a preferred concentration of 0.01%, and 1 mg to 40000 mg of pilocarpine hydrochloride or a similar miotic, with a preferred amount being 200 mg of pilocarpine hydrochloride, for a final concentration of 0.0001% to 4.0% or a preferred concentration of 0.02%.

Example 4

A fourth solution containing riboflavin may comprise a 1000 ml 0.01% to 0.9% sodium chloride solution, with a 0.6% sodium chloride solution being preferred, comprising 1 mg to 10000 mg of riboflavin, or a preferred amount being 4500 mg of riboflavin, for a final concentration of 0.0001% to 1.0%, or a preferred amount of 0.45%, and 1 mg to 10000 mg of proparacaine or a similar anesthetic, or a preferred amount of 2000 mg of proparacaine, for a final concentration of 0.0001% to 1.0% or a preferred concentration of 0.2%.

Example 5

A first anti-infective solution may comprise a 1000 ml 0.01 to a 0.9% sodium chloride solution, with a 0.45% sodium chloride solution being preferred, comprising 1 mg to 50000 mg of vancomycin or any similar antibiotic or anti-infective drug, with 25000 mg of vancomycin being preferred, for a final concentration of 0.0001% to 5.0%, or a preferred concentration of 2.5%, 1 mg to 10000 mg of proparacaine or other similar anesthetic, with a preferred amount being 100 mg of proparacaine, for a final concentration of 0.0001% to 1.0%, or a preferred concentration of 0.01%, and 1 mg to 3000 mg of benzalkonium chloride or a similar preservative, with a preferred amount of 500 mg of benzalkonium chloride, for a final concentration of 0.0001% to 0.3%, or a preferred concentration of 0.05%.

Example 6

A second anti-infective solution may comprise a 1000 ml 0.01 to a 0.9% sodium chloride solution, with a 0.45% sodium chloride solution being preferred, comprising 1 mg to 50000 mg of vancomycin or any similar antibiotic or anti-infective drug, with 25000 mg of vancomycin being preferred, for a final concentration of 0.0001% to 5.0%, or a preferred concentration of 2.5%, and 1 mg to 10000 mg of proparacaine or other similar anesthetic, with a preferred amount being 100 mg of proparacaine, for a final concentration of 0.0001% to 1.0%, or a preferred concentration of 0.01%.

Example 7

A third anti-infective solution may comprise a 1000 ml 0.01% to a 09% sodium chloride solution, with a 0.45% sodium chloride solution being preferred, comprising 1 mg to 10000 mg of amphotericin-B, with 5000 mg of amphotericin-B being preferred, for a final concentration of 0.0001% to 1.0%, or 0.5% being preferred, 1 mg to 10000 mg of proparacaine or a similar anesthetic, with 100 mg being preferred, for a final concentration of 0.0001% to 1.0%, with 0.01% being preferred, and 1 mg to 3000 mg of benzalkonium chloride, with 500 mg being preferred, for a final concentration of 0.0001% to 3.0%, or a preferred concentration of 0.05%.

Example 8

An anti-neoplasia solution may comprise a 1000 ml 0.01% to a 0.9% sodium chloride solution, with a 0.45% sodium chloride solution being preferred, comprising 1 mg to 2000 mg of mitomycin-C or a similar anti-neoplasia agent, with 1000 mg of mitomycin-C being preferred, for a final concentration of 0.0001% to 0.2%, with a preferred concentration of 0.1%, and 1 mg to 10000 mg of proparacaine or a similar anesthetic, or a preferred amount of 10 mg of proparacaine, for a final concentration of 0.0001% to 1.0%, or a preferred concentration of 0.001%.

Example 9

An anti-inflammatory solution may comprise a 1000 ml 0.01% to a 0.9% sodium chloride solution, with a 0.45% sodium chloride solution being preferred, comprising 1 mg to 10000 mg of dexamethasone sodium phosphate or a similar anti-inflammatory, with 1000 mg of dexamethasone sodium phosphate being preferred, for a final concentration of 0.0001% to 1.0%, with a preferred concentration of 0.1%, 1 mg to 10000 mg of proparacaine or a similar anesthetic, with 100 mg being preferred, for a final concentration of 0.0001% to 1.0%, and a preferred concentration of 0.01%, and 1 mg to 20000 mg of ketorolac tromethamine or similar non-steroidal agent, with an amount of 2000 mg being preferred, for a final concentration of 0.0001% to 2.0%, or a preferred concentration of 0.2%.

Referring now to the drawings, and more particularly to FIG. 1, there is initially illustrated a schematic cross-section of the human eye so as to effectively provide background information in order to enhance the understanding of the technique for delivering the medicinal solution of the present invention to the eye. More particularly, it is seen, for example, that the human eye is generally indicated by the reference character 10, and that the eye 10 comprises the cornea 12, which effectively covers, or is disposed in front of, the iris portion 14 of the eye and the lens 16, as well as the sclera 18. As has been noted hereinbefore, the objective of the present invention is to provide medicinal solutions to the corneal region 12 of the eye.

With reference now being made to FIGS. 2-5, a system for delivering medicinal solutions to a patient's eye 10 is disclosed and is generally indicated by the reference character 100. More particularly, and as can best be seen in FIG. 5, it is seen that a scleral contact lens 102, having an irrigation fluid supply tube 104 attached thereto so as to effectively comprise a contact lens similar to the well-known Morgan lens, is one of the primary components of the system which is used to deliver any one of the medicinal solutions of the present invention to the patient's eye 10 in a safe, comfortable, and efficient manner. It is to be noted, as in the case of the Morgan lens, that the outer or external periphery of the scleral contact lens 102 may have a complex cross-sectional configuration in order to effectively accommodate the change in shape and relative steepness characteristic of the cornea 12 with respect to the shape and relative steepness of the sclera 18, as can readily be appreciated from FIG. 1. In addition to the scleral contact lens 102, with the irrigation fluid supply tube 104 attached thereto, a porous corneal sponge 106, which may be fabricated from a suitable cellulose or similar material, is operatively associated with the scleral contact lens 102.

Figure 2:
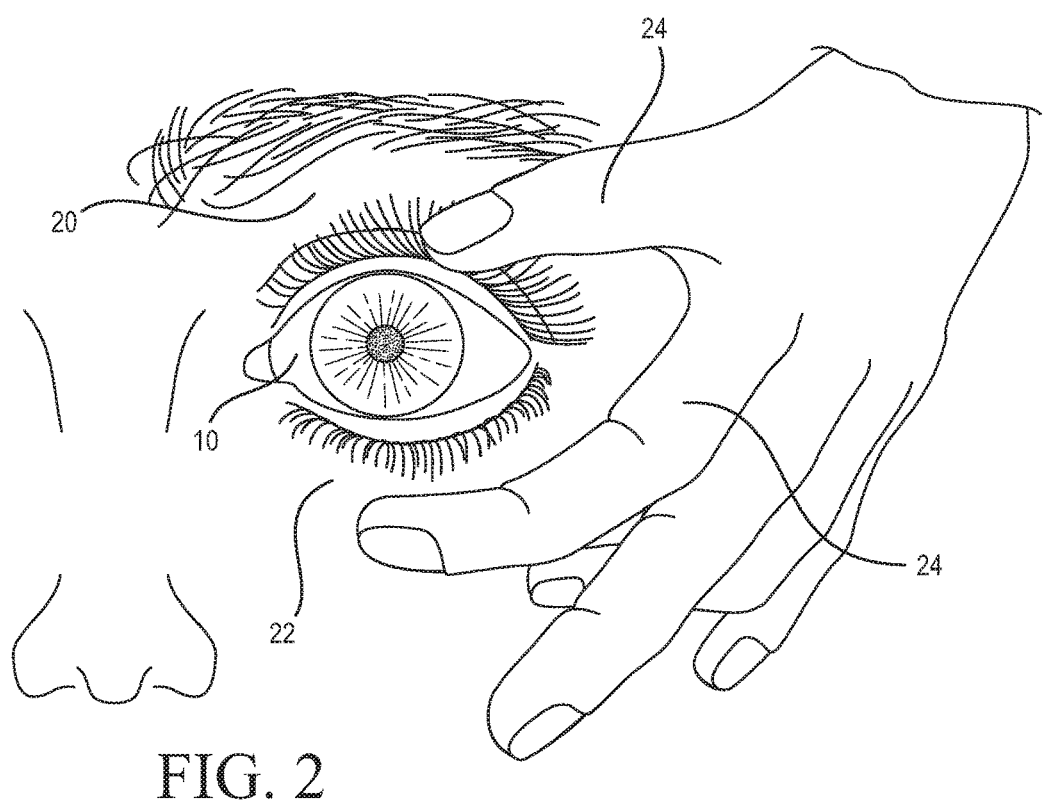
FIG. 2 is a schematic partial front view of a patient's face wherein the first step of the procedure for administering the medicinal solution of the present invention is illustrated as comprising the holding open of the patient's eyelids by means of the fingertips of the doctor or technician who will be performing the medicinal application procedure.
Figures 3A, 3B, 3C:
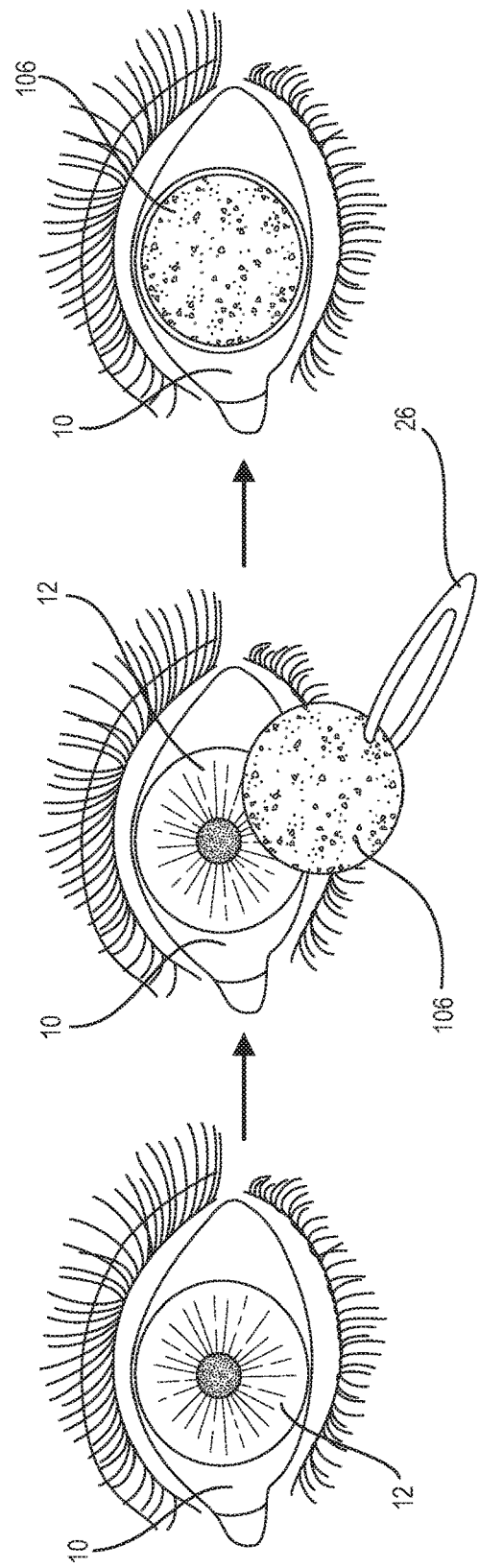
FIGS. 3a,3b,3c are serial schematic views showing the placement of a sponge on the corneal surface of the patient's eye by means of, for example, the use of a forceps, wherein the sponge has had a predetermined amount of the medicinal solution of the present invention, to be delivered to the eye in accordance with the medicinal application procedure, already impregnated therein.
Figure 4:
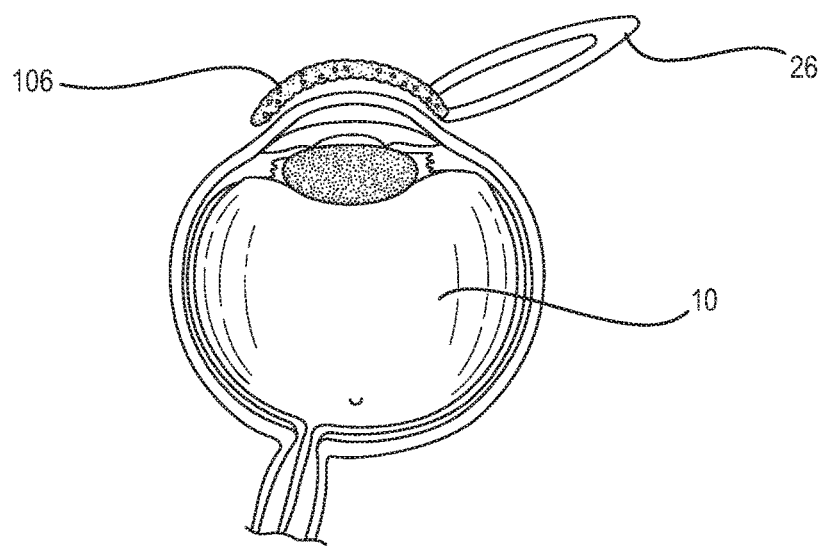
FIG. 4 is a top plan view of the patient's eyeball schematically illustrating the placement of the sponge, in a manner corresponding to that illustrated within FIGS. 3b,3c, upon the patient's eye by means of the forceps.
Figure 5:
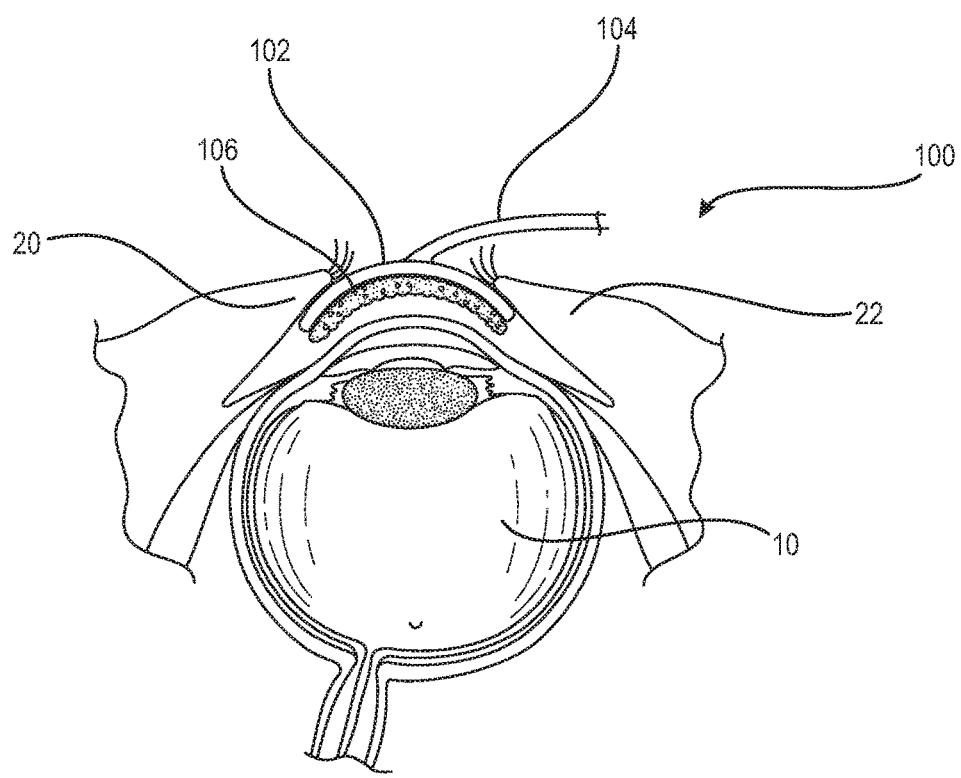
FIG. 5 is a top plan view of the patient's eyeball, similar to that of FIG. 4, showing however the eyelids being moved to their closed position, after the scleral lens, and the irrigation fluid supply tube attached thereto, has been disposed atop the sponge, so as to effectively entrap both the sponge and the scleral lens beneath the eyelids whereby the sponge and scleral lens can effectively be retained in position upon the corneal surface of the eye in preparation for the medicinal solution of the present invention to be conducted toward and into the sponge.

With reference initially being made to FIG. 2, the upper and lower eyelids 20,22 of the patient's eye 10 to be treated are initially held open by means of the fingertips 24 of the doctor or technician performing the treatment method, technique, or procedure, and the medicinal solution of the present invention, comprising riboflavin or other medication, and a topical anesthesia, is applied to the cornea of the eye. The topical anesthesia may comprise any of the aforenoted well known anesthesia commonly employed under such conditions such as, for example, tetracaine, proparacaine, lidocaine, and the like. The sponge 106, containing a small amount of the medicinal solution to be administered or delivered to the cornea 12 of the eye 10, is then applied to the surface of the eye 10 and centered over the cornea 12 of the eye 10 by using, for example, surgical forceps 26, as can best be seen in FIGS. 3b,3c, and 4. If desired, the sponge 106 can briefly be used to massage the surface of the eye 10 so as to remove any mucous or native tear film that might otherwise slow penetration of the medicinal solution to be administered or delivered to the cornea 12 of the eye 10. The scleral contact lens 102, with the irrigation fluid supply tube 104 attached thereto, is then effectively placed over the sponge 106, as illustrated within FIG. 5, care being taken to ensure that the sponge 106 and the scleral contact lens 102 are effectively centered upon, or seated or mounted directly over the cornea 12 of the eye 10. In addition, it is important to gently push or depress the scleral contact lens 102, with its irrigation fluid supply tube 104 attached thereto, onto the sponge 106 such that the sponge 106 is effectively disposed upon the cornea 12 of the eye 10 in a trapped state between the surface of the eye 10 and the scleral contact lens 102. At this point in time, the patient's eyelids 20,22 can then be closed so as to, in turn, effectively entrap and retain both the sponge 106 and the lens 102 upon the corneal surface of the eye 10.

In addition to the foregoing, and with reference being made to FIGS. 6 and 7, a syringe 108, containing the medicinal solution of the present invention and to be administered or delivered to the patient's eye 10, is operatively connected to the free end of the irrigation fluid supply tube 104. One of the objectives of the present invention is to provide a relatively low and constant volume of a high concentration of the medicinal solution to be administered or delivered to the eye 10. Accordingly, a suitable control device 110 is interposed between the syringe 108 and the scleral contact lens 102 so as to in fact control the volume flow and line pressure within the irrigation fluid supply tube 104. The control device 110 may be, for example, a stopcock type valve, a clamp, or any other suitable means which will limit or control the volume of the fluid flow of the medicinal solution of the present invention to the corneal sponge 106, and to the eye 10, to a predetermined degree, amount, or volume. In accordance with the usage of the noted components, the plunger 112 of the syringe 108 will be moved inwardly a predetermined amount so as to cause a relatively small amount of the medicinal solution to flow through the irrigation tube 104 and to effectively saturate the sponge 106 which is disposed over the cornea 12 of the eye 10. The stopcock or control device 110 is then adjusted, effectively trapping or controlling the flow of the medicinal solution within the system between the stopcock 110 and the sponge 106. Over time, tears within the patient's eye may tend to dilute the medicinal solution being delivered to the eye whereupon, in accordance with an additional step of the noted technique, the stopcock 110 will be opened or expanded, the plunger 112 of the syringe 108 will be pushed further a predetermined amount into the syringe 108, and an additional amount of the high concentration medicinal solution will again be delivered to the sponge 106 so as to maintain the same saturated with the medicinal solution being used to treat the eye 10. The stopcock 110 will then be adjusted again so as to control the flow of the medicinal solution to the desired degree. It will be noted that all during this process or procedure, the patient is disposed in a reclined position, with his or her eyelids closed, so as to enhance the comfort level of the patient as much as possible throughout the entire treatment procedure. The unique compositions of the present invention, namely a solution containing a suitable medication and an anesthetic, can aid in maintaining that comfort and increasing the penetration of the active ingredients while also delivering the other components of the solution which are unique to the needs of the patient.

In accordance with additional or alternative embodiments of the aforenoted system for implementing the aforenoted procedure, it is to be noted that the scleral lens 102 may effectively be eliminated from the system as illustrated, for example, within FIG. 6, whereby the irrigation fluid supply tube 204 is fluidically connected directly to the sponge 206 by any suitable means, such as, for example, a suitable adhesive or other similar fixation means. This second embodiment is illustrated, for example, within FIG. 8, wherein, in accordance with this second embodiment system 200, component parts have been provided with similar reference characters although they are within the 200 series. Still further, it is also to be noted, as can readily be appreciated from FIGS. 5-8, that the first and second embodiments of the system 100,200 comprised the use of a single irrigation fluid supply tube 104,204 which was fixedly connected to a central axial portion of the scleral lens 102 or to the central axial portion of the corneal sponge 206. However, as illustrated within FIG. 9, a third embodiment of a system or apparatus which may be employed to deliver the medicinal solution of the present invention is generally indicated by the reference character 300, and in lieu of the use of a single irrigation fluid supply tube 104,204, a plurality of irrigation fluid supply tubes 304a-304e may be integrally connected at first end portions thereof to a main irrigation fluid supply tube 304 and may be fluidically connected at second opposite end portions thereof to the scleral lens 302 or to the corneal sponge 306 so as to ensure the uniform distribution and supply of the medicinal solution being delivered to the eye 10.

Figure 9:
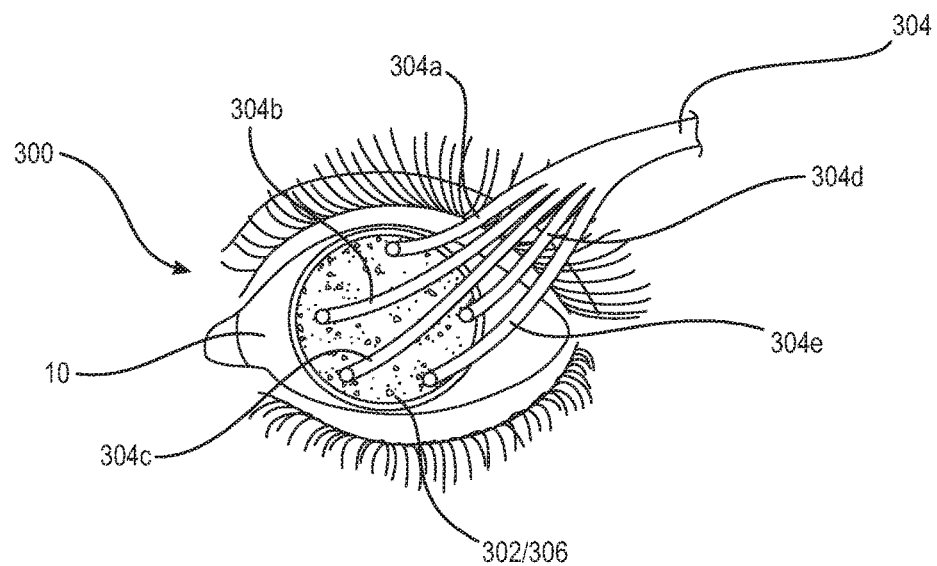
FIG. 9 is an external plan view of a third embodiment of medicinal solution application apparatus wherein the scleral lens has a multiplicity of irrigation fluid supply tubes having first end portions thereof connected to the scleral lens while second end portions of the multiplicity of irrigation fluid supply tubes are operatively connected to a single or main irrigation fluid supply tube which is adapted to be operatively connected to a syringe/plunger/stopcock assembly similar to that shown in FIG. 5, whereby the multiplicity of irrigation fluid supply tubes are disposed within an equiangular circumferentially spaced manner around the scleral lens so as to simultaneously provide the medicinal solution to the underlying sponge at equiangularly spaced locations of the sponge so as to effectively ensure that all regions of the sponge are in fact provided with a predetermined saturation volume of the medicinal solution to, in turn, be delivered to the cornea of the eye.

As can readily be seen and appreciated from FIG. 9, the second opposite end portions of the plurality of irrigation fluid supply tubes 304a-304e that are fluidically connected to the scleral lens 302 or to the corneal sponge 306 are fixedly connected to the scleral lens 302 or to the corneal sponge 306 at various locations which are optimally arranged in an equiangular circumferentially spaced manner so as to in fact ensure that the medicinal solution being delivered or administered to the eye 10 is in fact uniformly distributed to all regions of the corneal sponge so as to, in turn, ensure that all regions of the corneal sponge are uniformly saturated with the medicinal solution. It is to be noted that while an irrigation fluid supply tube is not illustrated within this embodiment as extending toward and being connected to the axially central portion of the scleral lens 302 or corneal sponge 306, such is in fact to be recognized as an additional possibility in order to ensure the aforenoted objective concerning the equal or uniform distribution of the medicinal solution to all regions of the scleral lens 302 or corneal sponge 306, such an axially connected irrigation fluid supply tube having been omitted merely for clarity purposes of the drawing figure. It is lastly to be noted that component parts of the third embodiment system 300 that correspond to similar component parts of the first and second embodiment systems 100,200 have been provided with similar reference characters except that they are within the 300 series.

Figure 10:
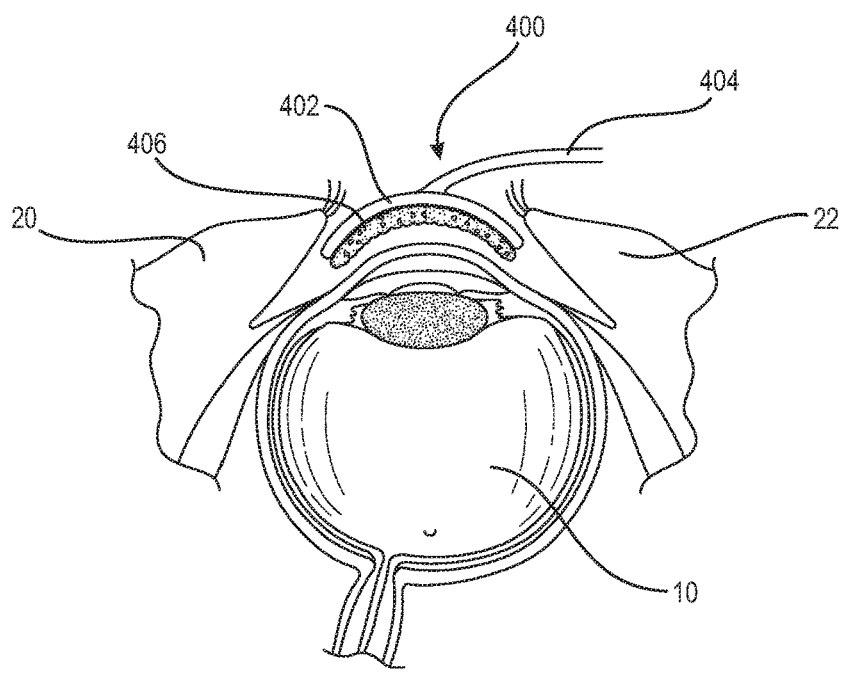
FIG. 10 is a top plan view of the patient's eyeball, similar to that of FIG. 5, showing however the instance wherein the scleral lens and the sponge components comprise an integral one-piece assembly and wherein the eyelids of the patient have been moved to their closed position, after the assembly comprising the scleral lens, the irrigation fluid supply tube attached thereto, and the sponge, have been disposed onto the surface of the eye so as to effectively entrap both the sponge and the scleral lens beneath the eyelids whereby the sponge and scleral lens assembly can effectively be retained in position upon the corneal surface of the eye in preparation for the medicinal solution application procedure.

Still yet further, as can be readily seen or appreciated from FIG. 10, in lieu of the scleral lens and the corneal sponge comprising separate components that are physically brought into contact with each other, in accordance with a fourth embodiment of a system or apparatus which may be utilized to deliver the medicinal solution of the present invention to the eye 10 and which is generally indicated by the reference character 400, the scleral lens 402 and the corneal sponge 404 may be integrally affixed together as a one-piece assembly whereby the combined device can be disposed over the cornea 12 of the eye 10 and then entrapped and retained upon the corneal surface of the eye 10 by means of the closed eyelids 20, 22.

Obviously, many variations and modifications of the present invention are possible in light of the above teachings, and it is to be construed that such variations and modifications are effectively to be included in conjunction with the claimed medicinal solution. For example, it is to be noted that the corneal sponges may comprise sponges having different thickness dimensions, different sizes, and may be fabricated from different materials comprising different porosity characteristics so as to predetermine saturation volumes and retention times with respect to the medicinal solutions being delivered to the cornea. The differently-sized corneal sponges can of course be used, for example, depending upon the size of the corneal region being treated. Still further, the corneal sponge can have a diametrical extent which is larger than that of the cornea per se whereby the outer peripheral edge portions of the corneal sponge will effectively be disposed in contact with the sclera, and in this manner, the eyelids will assuredly retain the corneal sponge is contact with the corneal surface of the eye when the patient's eyelids are moved to their closed positions. In a similar manner, the syringes may be characterized by different sizes so as to accommodate various volumes of the medicinal solution to be delivered. Still yet further, while the disclosed system has been implemented for the treatment of one eye, the method, technique, or procedure can obviously be repeated for the patient's other eye, or yet alternatively, a bilateral embodiment of the system is envisioned such that both eyes of the patient can be treated simultaneously. After treatment of the particular eye has been completed, the scleral lens and the corneal sponge, or the corneal sponge alone if the scleral lens was omitted from the system and the irrigation fluid supply tube was connected directly to the sponge, is removed from the patient's eye in accordance with a procedure or technique which is effectively the reverse of that described hereinbefore in connection with initial treatment of the patient. It is also to be noted that because the solution is being continuously irrigated as compared to a single drop application, the concentration of the drug may effectively be lower as compared to that which would normally be used in connection with a single drop application and yet the desired results would nevertheless be achieved. It is lastly to be understood that within the scope of the appended claims, the present invention may comprise other medicinal solutions than as has been specifically described herein.

KEY TO REFERENCE NUMBERS IN THE DRAWINGS

10—EYE
12—CORNEA
14—IRIS
16—LENS
18—SCLERA
20—UPPER EYELID
22—LOWER EYELID
24—FINGERTIPS
26—SURGICAL FORCEPS
100—FIRST EMBODIMENT SYSTEM
102—SCLERAL LENS OF FIRST EMBODIMENT
104—IRRIGATION FLUID SUPPLY TUBE OF FIRST EMBODIMENT
106—CORNEAL SPONGE OF FIRST EMBODIMENT
108—SYRINGE OF FIRST EMBODIMENT
110—CONTROL DEVICE OF FIRST EMBODIMENT
112—PLUNGER OF SYRINGE OF FIRST EMBODIMENT
200—SECOND EMBODIMENT SYSTEM
204—IRRIGATION FLUID SUPPLY TUBE OF SECOND EMBODIMENT
206—CORNEAL SPONGE OF SECOND EMBODIMENT
300—THIRD EMBODIMENT SYSTEM
302—SCLERAL LENS OF THIRD EMBODIMENT
304—MAIN IRRIGATION FLUID SUPPLY TUBE OF THIRD EMBODIMENT
304a-304e—MULTIPLICITY OF IRRIGATION FLUID SUPPLY TUBES
306—CORNEAL SPONGE OF THIRD EMBODIMENT
400—FOURTH EMBODIMENT SYSTEM
402—SCLERAL LENS OF FOURTH EMBODIMENT
404—IRRIGATION FLUID SUPPLY TUBE OF FOURTH EMBODIMENT
406—CORNEAL SPONGE OF FOURTH EMBODIMENT

What is claimed as new and desired to be protected by Letters Patent of the United States of America, is:

1. A composition for the treatment of an ophthalmic malady for use prior to the use of collagen cross-linking techniques, comprising:
   an active ingredient selected from the group consisting of riboflavin, vancomycin, amphotericin-B, mytomycin, and dexamethasone, wherein the concentration of the active agent is between 0.0001% to 1%;
   an anesthetic selected from the group consisting of proparacaine, lidocaine, tetracaine, and bupivacaine wherein the concentration of the anesthetic is between 0.0001% to 1%;
   pilocarpine, wherein the concentration of said pilocarpine is between 0.0001% to 4%; and
   benzalkonium chloride, a preservative, wherein the concentration of said benzalkonium chloride is between 0.0001% to 4%;
   wherein said composition is suitable for continuous or pulse delivery to the eye.

2. The composition as set forth in claim 1, comprising:
   1 mg to 10000 mg of riboflavin for a final concentration of 0.0001% to 1.0%, 1 mg to 10000 mg of proparacaine for a final concentration of 0.0001% to 1.0%, 1 mg to 3000 mg of benzalkonium chloride for a final concentration of 0.0001% to 0.3%, 1 mg to 500 mg of naphazoline hydrochloride for a final concentration of 0.0001% to 0.05%, and 1 mg to 40000 mg of pilocarpine hydrochloride for a final concentration of 0.0001% to 4.0% in a 1000 ml of 0.01% to a 0.9% solution of sodium chloride.

3. The composition as set forth in claim 1, comprising:
1 mg to 10000 mg of riboflavin for a final concentration of 0.0001% to 1.0%, 1 mg to 10000 mg of proparacaine for a final concentration of 0.0001% to 1.0%, and 1 mg to 3000 mg of benzalkonium chloride for a final concentration of 0.0001% to 0.3% in a 1000 ml of 0.01% to 0.9% solution of sodium chloride.

4. The composition as set forth in claim comprising:
1 mg to 10000 mg of riboflavin for a final concentration of 0.0001% to 1.0%, 1 mg to 10000 mg of proparacaine for a final concentration of 0.0001% to 1.0%, 1 mg to 3000 mg of benzalkonium chloride for a final concentration of 0.0001% to 0.3%, and 1 mg to 40000 mg of pilocarpine hydrochloride for a final concentration of 0.0001% to 4.0% in a 1000 ml of 0.01% to a 0.9% solution of sodium chloride.

5. The composition as set forth in claim 1, comprising:
1 mg to 10000 mg of riboflavin for a final concentration of 0.0001% to 1.0%, and 1 mg to 10000 mg of proparacaine for a final concentration of 0.0001% to 1.0% in a 1000 ml of a 0.01% to a 0.9% solution of sodium chloride.

6. The composition as set forth in claim 1, comprising:
1 mg to 50000 mg of vancomycin for a final concentration of 0.0001% to 5.0%, 1 mg to 10000 mg of proparacaine for a final concentration of 0.0001% to 1.0%, and 1 mg to 3000 mg of benzalkonium chloride for a final concentration of 0.0001% to 0.3% in a 1000 ml of a 0.01% to a 0.9% solution of sodium chloride.

7. The composition as set forth in claim 1, comprising: 1 mg to 10000 mg of amphotericin-B for a final concentration of 0.0001% to 1.0%, 1 mg to 10000 mg of proparacaine for a final concentration of 0.0001% to 1.0%, and 1 mg to 3000 mg of benzalkonium chloride for a final concentration of 0.0001% to 0.3% in a 1000 ml of a 0.01% to a 0.9% solution of sodium chloride.

8. The composition as set forth in claim 1, comprising:
1 mg to 2000 mg of mitomycin-C for a final concentration of 0.0001% to 0.2% and 1 mg to 10000 mg of proparacaine for a final concentration of 0.0001% to 1.0% in a 1000 ml of a 0.01% to a 0.9% solution of sodium chloride.

9. The composition as set forth in claim 1, comprising:
1 mg to 10000 mg of dexamethasone sodium phosphate for a final concentration of 0.0001% to 1.0%, 1 mg to 10000 mg of proparacaine for a final concentration of 0.0001% to 1.0%, and 1 mg to 20000 mg of ketorolac tromethamine for a final concentration of 0.0001% to 2.0%, in a 1000 ml of a 0.01% to a 0.9% solution of sodium chloride.

10. The composition as set forth in claim 1, further comprising:
a medication for causing pupillary constriction.

11. The composition as set forth in claim 2, comprising:
6000 mg of riboflavin, for a final concentration of 0.6%, 1000 mg of proparacaine, for a final concentration of 0.1%, 500 mg of benzalkonium chloride for a final concentration of 0.05%, 50 mg of naphazoline hydrochloride for a final concentration of 0.005%, and 500 mg of pilocarpine hydrochloride for a final concentration of 0.05% in a 1000 ml of 0.45% solution of sodium chloride.

12. The composition of claim 3, comprising:
5500 mg of riboflavin, for a final concentration of 0.55%, 500 mg of proparacaine, for a final concentration of 0.05%, and 250 mg of benzalkonium chloride for a final concentration of 0.025% in a 1000 ml of 0.45% solution of sodium chloride.

13. The composition as set forth in claim 4, comprising:
2500 mg of riboflavin for a final concentration of 0.25%, 750 mg of proparacaine for a final concentration of 0.075%, 100 mg of benzalkonium chloride for a final concentration of 0.01%, and 200 mg of pilocarpine hydrochloride for a final concentration of 0.02% in a 1000 ml of a 0.45% solution of sodium chloride.

14. The composition of claim 5, comprising:
4500 mg of riboflavin for a final concentration of o.45%, and 2000 mg of proparacaine for a final concentration of 0.2% in a 1000 ml of a 0.6% solution of sodium chloride.

15. The composition of claim 6, comprising: 25000 mg of vancomycin for a final concentration of 2.5%, 100 mg of proparacaine for a final concentration of 0.01%, and 500 mg of benzalkonium chloride for a final concentration of 0.05% in a 1000 ml of a 0.45% solution of sodium chloride.

16. The composition as set forth in claim 7, comprising:
5000 mg of amphotericin-B for a final concentration of 0.5%, 100 mg of proparacaine for a final concentration of 0.01%, and 500 mg of benzalkonium chloride for a final concentration of 0.05% in a 1000 ml of a 0.45% solution of sodium chloride.

17. The composition as set forth in claim 8, comprising:
1000 mg of mitomycin-C for a final concentration of 0.1%, and 10 mg of proparacaine for a final concentration of 0.001% in a 1000 ml of a 0.45% solution of sodium chloride.

18. The composition of claim 9, comprising: 1000 mg of dexamethasone sodium phosphate for a final concentration of 0.1%, 100 mg of proparacaine for a final concentration of 0.01%, and 2000 mg of ketorolac tromethamine for a final concentration of 0.2% in a 1000 ml of a 0.45% solution of sodium chloride.

* * * * *